United States Patent [19]

Noir et al.

[11] Patent Number: 4,635,630
[45] Date of Patent: Jan. 13, 1987

[54] APPARATUS FOR HEAT THERAPY BY INHALATION

[75] Inventors: Dominique Noir, Aubonne; Yves Trouilhet, Vesenaz, both of Switzerland

[73] Assignee: Battelle Memorial Institute, Carouge, Switzerland

[21] Appl. No.: 750,606

[22] PCT Filed: Oct. 16, 1984

[86] PCT No.: PCT/CH84/00168
§ 371 Date: Jun. 19, 1985
§ 102(e) Date: Jun. 19, 1985

[87] PCT Pub. No.: WO85/01661
PCT Pub. Date: Apr. 25, 1985

[30] Foreign Application Priority Data
Oct. 20, 1983 [CH] Switzerland .......... 5708/83

[51] Int. Cl.4 .......... A61M 15/00
[52] U.S. Cl. .......... 128/203.26; 128/204.17
[58] Field of Search .......... 128/203.16, 203.17, 128/203.26, 203.27, 204.17, 200.21, 203.25

[56] References Cited

U.S. PATENT DOCUMENTS

| | | | |
|---|---|---|---|
| 286,666 | 10/1883 | Willis | 128/203.16 |
| 384,777 | 6/1888 | Ochs | 128/203.16 |
| 837,171 | 11/1906 | Wolfe | 128/203.25 |
| 1,981,765 | 11/1934 | Weiss | 128/203.17 |
| 2,023,324 | 12/1935 | Johnson et al. | 128/203.17 |
| 2,040,630 | 5/1936 | Silten | 128/200.21 |
| 2,818,486 | 12/1957 | Schmitt et al. | |
| 3,045,670 | 7/1962 | Hirtz et al. | |
| 3,098,926 | 7/1963 | Katzman | |
| 3,894,537 | 7/1975 | Camp | |
| 3,949,743 | 4/1976 | Shanbrom | 128/203.17 |
| 3,990,441 | 11/1976 | Hoyt et al. | |
| 4,182,325 | 1/1980 | Camp | |
| 4,195,044 | 3/1980 | Miller | |
| 4,200,093 | 4/1980 | Camp | |
| 4,268,460 | 5/1981 | Boiarski et al. | |
| 4,318,397 | 3/1982 | Kobayashi | |

FOREIGN PATENT DOCUMENTS

| | | |
|---|---|---|
| 0055537 | 7/1982 | European Pat. Off. |
| 3045351 | 9/1981 | Fed. Rep. of Germany |
| 906623 | 1/1946 | France |
| 1091247 | 4/1955 | France |
| 78035 | 7/1960 | France |
| 2267831 | 11/1975 | France |
| 2082462 | 3/1982 | United Kingdom |

Primary Examiner—Henry J. Recla
Attorney, Agent, or Firm—Cushman, Darby & Cushman

[57] ABSTRACT

This apparatus incorporates an enclosure (1) designed to contain water in which are immersed two electrodes (9,10) connected to an alternating current source (S). A tube (13) terminating in a nozzle (14) connect the top of this enclosure (1) to a venturi (15) which is connected upstream to the atmosphere and downstream to an inhalation mask (17), so as to form an air/water vapor mixture at a controlled temperature.

1 Claim, 3 Drawing Figures

U.S. Patent   Jan. 13, 1987   4,635,630
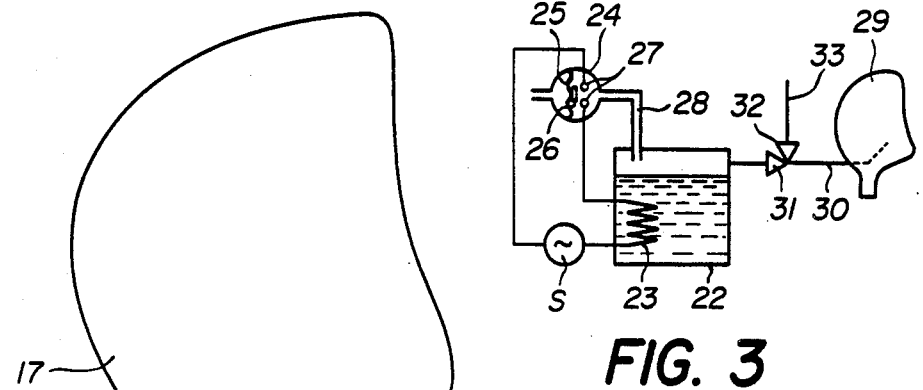
FIG. 3
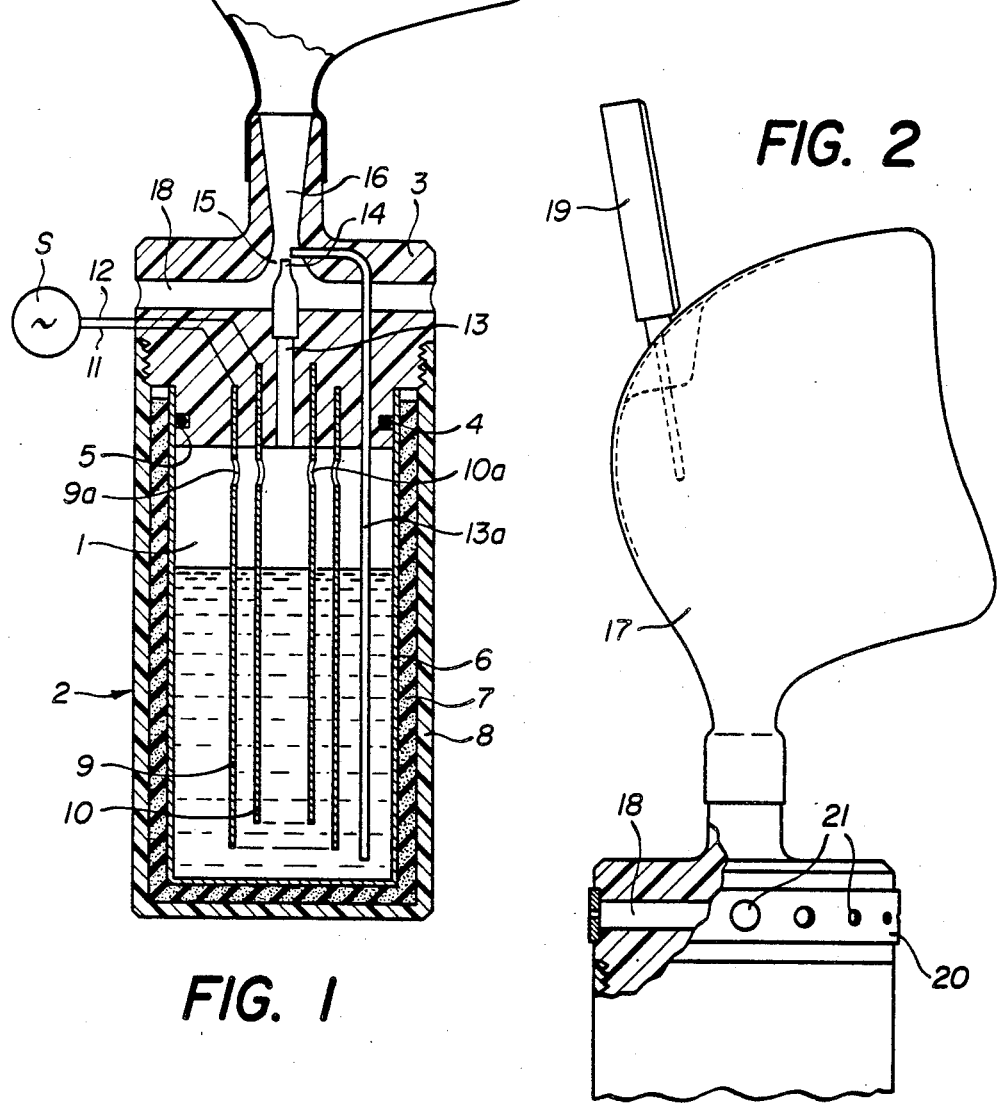
FIG. 2
FIG. 1

APPARATUS FOR HEAT THERAPY BY INHALATION

The present invention relates to an apparatus for heat therapy by inhalation.

The work of Professor André Lwoff has shown that the development of a virus depends on the temperature, which can be characterised in three zones: optimal, infra- and supra-optimal. At supra-optimal temperatures, the viral genetic material is destroyed by the lysozomal enzymes which are prematurely released, and the development of the virus is blocked. This work forms the subject of a report to the Académie des Sciences de Paris (Academy of Sciences of Paris), vol. 291 (8 Dec. 1980) series D-957.

On the basis of this work, a Franco-Israeli team of research workers at the Weizmann and Pasteur Institutes developed a heat therapy of infectious coryza and persistent allergic rhinitis. For this purpose, a so-called "rhinotherme" apparatus was designed and formed the subject of patent application FR No. 2,399,851. The clinical trials based on this heat therapy enabled suspension of the symptoms of the disease to be achieved for a long period in a large percentage of the patients, especially in patients suffering from persistent rhinitis which resisted any other treatments.

Although these results are encouraging, the complexity and cost of the apparatus developed for this purpose make this therapy inaccessible to the general public, so that this simple and wholly natural therapy is, in practice, only used at the very most in the hospital situation. Now it is clear that an apparatus of simpler design, sold at a reasonable price, would naturally find its place in any family medicine cabinet in the same way as electric tooth-brushes or other apparatus for care of the gums. Widespread distribution of such an apparatus could have beneficial effects both on health insurance resources and on the economy generally, taking account of the frequency of these viral complaints which, during some winters, cause the loss of a large number of working days.

The object of the present invention is, specifically, an apparatus for heat therapy by inhalation which is simple in design and safe in operation, the price of which makes it suitable as an apparatus for home use.

For this purpose, the present invention has as its subject an apparatus for heat therapy by inhalation according to claim 1.

The simplicity of this apparatus results from its design, which does not involve any moving parts, the motive component consisting either of steam under pressure which results from heating water and feeds a venturi, or of the partial vacuum which results from breathing in. Since the operating parameters are essentially constant, the temperature of the air/steam mixture inhaled can be fixed by the design.

The attached drawing show diagrammatically, and by way of example, two embodiments and a variant of the apparatus which is the subject of the present invention.

FIG. 1 is a sectional view in elevation of one of these embodiments.

FIG. 2 is a partial view of a variant in elevation, partially cut away.

FIG. 3 is a diagram of the second embodiment.

The apparatus illustrated in FIG. 1 incorporates an enclosure 1 formed by a cylindrical container 2 which is closed by a stopper 3 screwed onto this container. An O-ring sealing gasket 4 situated in a groove 5 made in the side of this stopper 3 serves to effect the sealing between the stopper 3 and the cylindrical container 2.

The wall of the container 2 incorporates an inner stainless steel part 6 surrounded by a thermally insulating layer 7 and an external envelope 8 which can, for example, be of plastic.

The stopper 3 carries, concentric with its axis of revolution, two coaxial tubes 9 and 10 made of stainless steel, non-corroding alloy or platinised titanium, for example. These tubes are connected by two conductors, 11 and 12 respectively, to an alternating current source S, and have perforations, 9a and 10a respectively, at the top. These tubes, which act as electrodes for heating undistilled water, can obviously be replaced by two simple rods (not shown) which advantageously terminate at the bottom end in two spheres or discs in order to increase the conducting surface of the electrodes at the bottom of the container, so that the heating is less dependent on the water level, the water constituting both the heating resistance and the product distributed in vapour and droplet form.

A tube 13 passes axially through the stopper 3 and terminates in a nozzle 14 which extends into the neck of a venturi 15 formed at the junction between a tube 16, which opens into an inhalation mask 17, and a tube 18 which passes diametrically through the stopper 3 to allow the neck of the venturi 15 to communicate with the atmosphere. A capillary tube 13a connects the bottom of the container 2 to the nozzle 14. It should moreover be pointed out that the mask 17 constitutes an example. It could be replaced by two tubes designed to be placed directly in the nozzles and to avoid harming the skin of the face through the effect of steam.

The apparatus described operates in the following manner: water is poured into the container 2 up to a level marked on the inner wall 6 of this container, this level being situated at a certain distance, for example 3 cm, from the lower face of the stopper 3. The stopper 3, with its tubular electrodes 9 and 10, is screwed onto the container 2 and the electrodes are connected to the alternating current source S. The passage of current between these electrodes causes the water to be heated. The openings 9a and 10a enable the water to be maintained at the same level in the different zones of the container 2, and enables the steam to be conveyed towards the tube 13 When the water boils after about 1 to 2 minutes, the steam produced escapes under pressure through the tube 13 and nozzle 14 and creates a partial vacuum in the neck of the venturi 15, which draws air in. The adjustment of the venturi is carried out in such a manner that the mixing of the ambient air at about 20° C. and water vapour at 100° C. gives air which is almost saturated with water at about 43° C., with a flow rate of the order of 45 l/min. This constant flow rate represents $\frac{3}{4}$ litre per second, which corresponds to the volume inhaled by an adult individual.

The water vapour reaches the nozzle 14 at a pressure of the order of $10^3$ to $10^4$ Pa. The nozzle 14 has a diameter of 0.5 to 2 mm and the speed of the vapour is of the order of 50–200 m/s. The flow rate of the vapour is of the order of 0.33 $m^3$/h with a density of 0.6 kg/$m^3$. If it is taken into account that the treatment lasts about half an hour, the consumption of water is of the order of 1 dl, so that the capacity of the enclosure 1 is of the order of 150 $cm^3$.

The air drawn in by the water vapour is ambient air at about 20° C. at the approximate rate of 2 m³/h or about 2.6 kg/h. This gives a mass flow rate of air saturated with water vapour at 43° C. of 2.8 kg/h. As a result of the overpressure which exists in the container 2 and the partial vacuum which exists at the nozzle 14, a certain amount of water is atomised at the outlet of the tube 13a in the form of droplets from 2 to 20 μm in diameter which are intended for deposition on the nasal mucosa and for improving the efficiency of heating of this mucosa, which has to be suitably moistened.

The variant illustrated in FIG. 2 incorporates in addition a device for measuring the temperature, consisting for example of a bimetallic strip thermometer 19 arranged in the inhalation mask 17, the display dial of the thermometer being visible to the user during inhalation, which enables him to ensure that the treatment is progressing correctly.

This measuring device is completed by an adjustment member which comprises a ring 20 mounted to rotate around the part of the stopper 3 through which the diametral tube 18 passes. This ring 20 has two series of openings 21, the diameters of which decrease in the same direction. The openings which have equivalent diameters in each series are diametrically opposed around the ring 20, so that they can be placed simultaneously opposite the two ends of the diametral tube 18. By means of this adjustment ring 20, the user can take action in the case where the temperature of the atmosphere created inside the inhalation mask 17 is incorrect. If this temperature is too high, he will turn the ring 20 so as to situate openings 21 of larger diameter at the ends of the diametral tube 18, so that the proportion of air drawn in by the venturi 15 will increase and the temperature of the air/water vapour mixture will decrease. In the opposite case, he will situate openings 21 of smaller diameter opposite the diametral tube 18 and the mixture temperature will increase. In fact, the apparatus will be positively calibrated to deliver a mixture at 43° C. starting with air at 20° C., which represents the commonest case of use. Nevertheless, the measuring and adjustment device enables monitoring to be carried out and the temperature to be adjusted in the case of operation from other conditions, when the ambient temperature is different from 20° C., that of the vapour remaining constant.

According to the invention, the apparatus for heat therapy by inhalation is hence extremely simple, which makes it suitable as an ideal apparatus for home use, thus taking its place in the family medicine cabinet. Not only does its simple design enable it to be produced at a reasonable price, but it requires practically no maintenance apart from elementary hygiene measures which can consist either in cleaning the mask 17, or in replacing it after each use or after the series of treatments required for curing one and the same patient.

To heat the water by means of the electrodes described and using the conductivity of the water, it is appropriate to take a tap water the conductivity of which can vary between 1,000 μS/cm and 4,000 μS/cm.

When the conductivity of the water is too low for the area of the electrodes, it can be increased by adding an acid or NaCl.

In this case, the conductivity of the solution will increase proportionately with the evaporation of the water, since the concentration of the solution will increase proportionately with this evaporation. Given that the electrode area submerged decreases as the level of the solution becomes lower, a substantially constant activity is obtained.

The use of tap water does not pose any particular problems in relation to bacteria, since this water is heated to the boiling point to produce the steam required for the apparatus to work properly. The furring which can result from the use of hard water can be dissolved by a 10% strength acetic acid solution. The use of distilled water with added NaCl is a measure which enables the problem of furring to be eliminated.

By way of example, the dimensioning of the electrodes can be as follows:

assuming a flow rate of air saturated with steam of 0.75 l/s, corresponding to 2.86 kg/h, the mass flow rate of water according to the Mollier diagram will be:

$$M = 0.18 \text{ kg/h}$$

the necessary electrical power is $$\dot{Q} = 0.18 \frac{\text{kg}}{\text{h}} \times 2592 \frac{kJ}{\text{kg}} \times \frac{\text{h}}{3{,}600s} = 130 \text{ W}$$

$$\text{which gives } I = \frac{130 \text{ W}}{220 \text{ V}} = 0.59 \text{ A}$$

the resistance will have to be $$R = \frac{220 \text{ V}}{0.59 \text{ A}} = 372 \text{ ohms}$$

$$R = \frac{L}{\gamma S_e}$$

where $L$ = distance between electrodes $\gamma$ = conductivity $S_e$ = electrode area Given that, to avoid the effect of electrolysing the water, the current density $I/S \leqq 1{,}200 \text{ A/m}^2$, $$\text{if } \gamma = 1{,}000 \ \mu S/\text{cm} = 1{,}000 \frac{1}{M\Omega\text{cm}}$$

$$S_e = 5 \text{ cm}^2$$

$$L = S_e \gamma R = 5 \times 1{,}000 \times 10^{-6} \frac{1 \text{ cm}^2}{\Omega\text{cm}} \ 372 \text{ Ohms}$$

$$L = 1.86 \text{ cm.}$$

The calculation of the choice of dimensions should take account of a significant decrease in the activity from the start of vaporisation, as a result of the presence of bubbles of steam which decrease the useful wet area of the electrodes.

In addition to modifying the acidity of the water, it is of course also possible to act, for example, on the gap between the electrodes. Although the heating system consists advantageously of two electrodes connected to an alternating current source, which has the advantage of being cheap and of avoiding any accidental overheating by virtue of there being no heating in the absence of water, it is however possible to consider other types of heating, such as heating by the Joule effect which consists in immersing an electrical resistance in the enclosure 1 in place of the electrodes.

The second embodiment illustrated very schematically in FIG. 3 incorporates an enclosure 22 in which a heating element 23 is immersed in the water. This heating element, which can be composed of two electrodes and water of low conductivity as in the example described above, is connected to a current source S through a compactor comprising a casing 24 divided into two parts by an elastic membrane 25 bearing metal cap 26. One of the conductors connecting the current source S to the heating element 23 passes through the casing 24 and is interrupted between two terminals 27. The part of the casing 24 containing the terminals 27 is connected, through a tube 28, to the top of the enclosure 22, while the other part of this same casing 24 communicates with the atmosphere so that the position of the metal cap 26 relative to the terminals 27 depends on the pressure difference between the atmosphere and the enclosure 22.

The top of this enclosure 22 is again connected to an inhalation mask 29 through a tube 30, along which the flow of the steam produced in the enclosure 22 is controlled by a one-way valve 31. This valve is normally closed when the pressure in the tube 30 is equal on the upstream and downstream sides, and opens when the pressure is higher upstream than downstream so as to permit the vapour to flow in the direction of the inhalation mask 29. A second valve 32 controls the flow through a tube 33 which communicates with the atmosphere and opens into the tube 30 downstream from the valve 31. This valve 32 is identical to the preceding valve so that it likewise opens when the pressure prevailing downstream of this valve 32 is lower than atmospheric pressure. Each valve 31, 32 can be associated with means for adjusting the cross-section of flow in the respective types 30 and 33.

The apparatus according to this embodiment operates in the following manner: when the pressure is identical on both sides of the membrane 25, the latter brings the metal cap 26 to bear against the terminals 27, applying voltage to the heating element 23. When the water present in the enclosure 22 boils and gives off steam, the pressure increases slightly and the membrane 25 then separates the metal cap 26 from the terminals 27, interrupting the supply to the heating element 23. The apparatus is then ready for operation.

As soon as a partial vacuum prevails in the downstream part of the tube 30 as a result of breathing in from the mask, the valves 31 and 32 open simultaneously, thereby allowing steam and air to pass through in proportions which depend on their respective cross-sections of flow.

As soon as the pressure in the enclosure 22 is reduced as a result of the flow of steam towards the inhalation mask 29, contact between the metal cap 26 and the terminals 27 is re-established and the heating of the water releases steam again. As soon as the user stops breathing in, the valves 31 and 32 close again and the production of steam in the enclosure 22 ceases as soon as the pressure slightly exceeds atmospheric pressure. This embodiment differs from the above embodiment essentially in respect of the discontinuous mode of operation, the flow of the air/steam mixture only being produced as a result of a partial vacuum in the tube 30 generated by the user breathing in at the upstream end of this tube. The use of two electrodes and of the resistance of the water as a heating element has the advantage of virtually zero inertia, providing an almost instantaneous response time.

As a variant, it is furthermore possible to eliminate the contact controlled by the membrane 25 and to connect the top of the enclosure 22 to the atmosphere through a calibrated vent (not shown) designed to maintain a substantially constant pressure in this enclosure 22, this pressure being chosen to be lower than the pressure at which the valve 31 opens.

We claim:

1. Apparatus for providing heat therapy by inhalation, comprising:
    wall means defining an enclosure for heating at its boiling temperature a quantum of aqueous liquid when contained therein to a level which incompletely fills said enclosure, leaving a headspace of said enclosure unfilled by aqueous liquid above said level;
    a tube having an inlet end and an outlet end, said inlet end of said tube opening into said headspace of said enclosure and said outlet end of said tube being provided with a nozzle;
    a pipe secured to said wall means and having an inlet end and an outlet end, said inlet end of said pipe being adapted to be open to the atmosphere, and said outlet end of said pipe including means adapted to provide from said headspace and from the atmosphere, in use, a hot, moist air mixture for inhalation by a user for providing heat therapy for the user;
    said pipe, intermediate said inlet and said outlet ends thereof having surface means defining a neck of a venturi therein;
    said nozzle of said tube opening into said venturi neck, towards said outlet end of said pipe, so that as pressurized steam issues from said nozzle, atmospheric air will be drawn into said pipe through said inlet end of said pipe and form with said steam at said nozzle a hot, moist air mixture;
    said nozzle and said venturi neck being dimensioned to provide, in use, a hot moist air mixture having a temperature within the range of 38°–50° C.; and
    a second tube secured to said wall means and having an open inlet end disposed below said level in said enclosure and having an open outlet end disposed in said pipe adjacent said nozzle and being adapted to supply, in use, heated aqueous liquid drawn thereinto from said enclosure to said hot, moist air mixture for inhalation by the user, as droplets having sized in the range of 2–20 $\mu$m.

* * * * *